United States Patent
Kim

(12)
(10) Patent No.: US 6,713,091 B1
(45) Date of Patent: Mar. 30, 2004

(54) COMPOSITION FOR LOWERING THE CONCENTRATION OF ALCOHOL IN BLOOD CONTAINING EXTRACTS OF PEPINO AND METHOD FOR PRODUCING THE SAME

(76) Inventor: Chan Sik Kim, 29-4 Samsan-ri, Joma-myeon, Kimcheon-si, Kyungsangbuk-do (KR)

( * ) Notice: Subject to any disclaimer, the term of this patent is extended or adjusted under 35 U.S.C. 154(b) by 0 days.

(21) Appl. No.: 09/568,304

(22) Filed: May 9, 2000

(30) Foreign Application Priority Data

Jul. 5, 1999 (KR) ........................................ 1999-26841

(51) Int. Cl.⁷ .............................................. A61K 35/78
(52) U.S. Cl. ...................................................... 424/725
(58) Field of Search ........................ 426/590; 424/195.1, 424/725

(56) References Cited

U.S. PATENT DOCUMENTS 6,194,469 B1 * 2/2001 Nair et al. ................... 514/886

FOREIGN PATENT DOCUMENTS

| EP | 1 066 853 A1 | * | 10/2001 | |
|----|-----|---|---------|---|
| JP | 406014746 | * | 1/1994 | ............... 426/590 |
| JP | 409075045 A | * | 3/1997 | |
| JP | 01058952 A | * | 3/2001 | |

OTHER PUBLICATIONS

National Research Council; Lost Crops of the Incase Little–KNWN Plants of the Andes With Promise for Worldwide Cultivation; 1989; National Academy Press, Washington, D.C., pp. 279–305.*

Licorice; Encyclopedia Britannica Online, http://www.search.eb.com/bol/topic?eu=49298&sctn=1, Accessed May 11, 2001.*

Gruenwald ed. et al. PDR for Herbal Medicines; First Edition, 1998, pp. 875–877.*

Litvinenko et al. Flavonoids From the Aboveground Part of Glycyrrhiza Glabra; Rast. Resur. (1972), 8 (1) pp. 35–82 (Abstract provided only).*

Sishan et al. Two New Isoprenyl Flavonoids from the Leaves of Glycyrrhiza Uralensis; Chin. Chem. Lett. (1992), 3 (3), pp. 189–190 (Abstract provided only).*

Revilla et al. Comparison of Several Procedures Used for the Extraction of Anthocyanins From Red Grapes; J.Agric. Food Chem., 1998, 46 pp. 4592–4597.*

* cited by examiner

Primary Examiner—Christopher R. Tate
Assistant Examiner—Patricia D Patten
(74) Attorney, Agent, or Firm—Wood, Phillips, Katz, Clark & Mortimer

(57) ABSTRACT

This invention relates to a composition for lowering the concentration of alcohol in blood which comprises extracts of the leaves of the pepino, stalk and fruit of the pepino as an effective component, and method for the preparation thereof. The composition of the invention comprises mixing 60–70% by weight of the extracts of the leaves and the stalks of the pepino and licorice with 30–40% by weight of the extracts of the fruit of the pepino. The composition of the invention can be used as a beverage for curing a hangover, a drug for curing alcoholism or a diet food using dietary fiber.

7 Claims, 2 Drawing Sheets

COMPOSITION FOR LOWERING THE CONCENTRATION OF ALCOHOL IN BLOOD CONTAINING EXTRACTS OF PEPINO AND METHOD FOR PRODUCING THE SAME

BACKGROUND OF THE INVENTION

The invention relates to a composition for lowering the concentration of alcohol in blood which comprises extracts of the leaves, stalks and fruit of the pepino, a kind of fruit and vegetable, as an effective component, and method for the preparation thereof.

Modern men often consume too much alcohol in both social circumstances and in an effort to reduce the ever-increasing stresses of life. The results of drinking too much, together, are commonly known as a hangover. Some of those symptoms are, for example, headache, fatigue, abdominal distention, emesis and a general malaise. The hangover condition is caused by the following mechanism: alcohol absorbed into the body is absorbed in the gastrointestines or small intestines, and transferred into the liver through blood vessels; alcohol is oxidized into acetaldehyde by dehydrogenase, and finally, in the metabolic process the alcohol is divided into carbonic acid, gas and water. A disorder is generated in the metabolism process from the toxic function of the acetaldehyde. To cure the hangover, many products have been developed which purport to lower the concentration of alcohol in the blood. However, said products don't have a remarkable effect in curing the hangover and it cannot be determined whether or not they substantially lower the concentration of alcohol in the blood.

SUMMARY OF THE INVENTION

The present invention is contrived to address the above problems found with the currently ineffective products. Although it is prepared through a simple process, the effect of lowering blood alcohol levels is excellent.

The present invention provides a composition for lowering the concentration of alcohol in the blood which comprises extracts of the leaves, stalks and fruits of the pepino as an effective component.

The invention also provides the method for the preparation of the composition for lowering the concentration of alcohol in blood which comprises extracting the leaves or stalks of the pepino into water or alcohol; mixing these extracts with licorice forming a concentration of these; mixing these concentrates with the extracts of the pepino fruits and concentrating these.

The composition for lowering blood alcohol concentration of the invention may be used for various kinds of beverages, food and drugs.

DETAILED DESCRIPTION OF THE PREFERRED EMBODIMENTS

Figure 1:
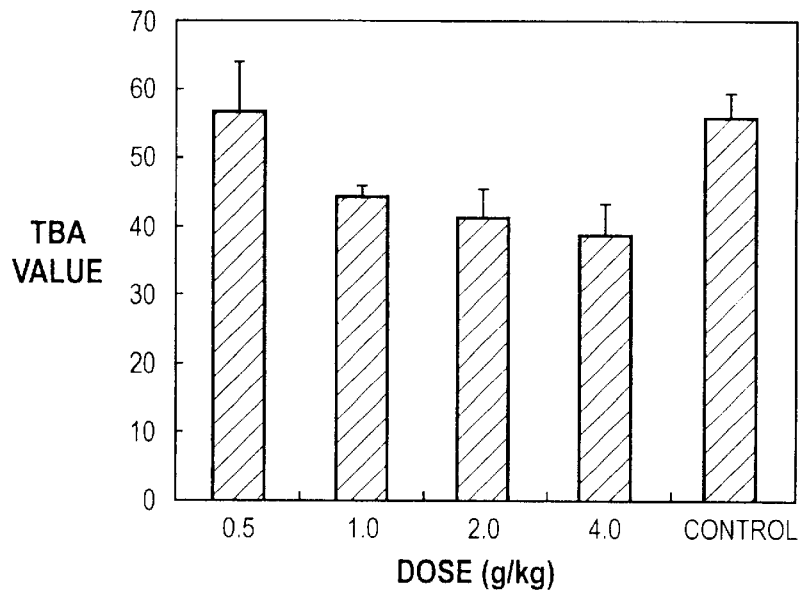
FIG. 1 is a graph showing the in vivo antioxidation action of the composition according to the invention.

Pepino, whose place of origin is South America, has leaves which are almost like a pimento. Its flowers are exactly like an eggplant. Its fruits are the same shape as a small eggplant having the size in the range of about 200–300 g, and its flesh is succose like watermelon. The fruit of the pepino is generally ingested as fruit. The leaves cannot be ingested because of their strong acerbity.

The invention is a composition for lowering the concentration of alcohol in blood, characterized in that comprises 60–70% by weight of the concentrates obtained by adding 30 g of licorice to 20 L of the extracts of the leaves and stalks of the pepino and then concentrating the results and 30 to 40% by weight of the extracts of the fruit, using the fruit, leaves and stalks of the pepino.

If the composition of the invention contains more than 40% by weight of the fruit extracts of pepino, the effect of lowering the concentration of alcohol in blood increases. However, the saccharinity is thereby higher and produces trouble with the digestive process. If it contains under 30% by weight of the fruit extracts of the pepino, the effect of lowering the concentration of alcohol in blood decreases.

If the composition of the invention contains more than 70% by weight of the extracts of the leaves and stalks of the pepino, the effect of lowering the concentration of alcohol in blood decreases. If it contains under 60% by weight of the fruit extracts of the pepino, it produces trouble with the digestive process.

The leaves and stalks of the pepino are comprised of 88.80% of water, 2.92% of dietary fiber and other components, thus it seems that such dietary fiber aids digestion.

It has not been known that the composition of the invention indicates the effect of lowering the concentration of alcohol in blood by any mechanism. However the effect is envisaged by means of the abundant asparagine acid, as shown by below tables 1 and 2, indicating the distribution of the amino acid components in the leaves and fruits of the pepino.

TABLE 1

| Amino acid analysis of fruit of pepino | |
|---|---|
| amino acid | content (mg %) (sample of pepino fruit per 100 g) |
| asparagine acid | 444.6 |
| glutamine acid | 138.2 |
| serine | 22.9 |
| glycine | 16.3 |
| histidine | 11.3 |
| threonine | 11.8 |
| arginine | 21.7 |
| alanine | 25.8 |
| proline | 15.7 |
| tyrosine | 13.7 |
| cysteine | 0.0 |
| valine | 16.7 |
| methionine | 3.6 |
| isoleucine | 15.4 |
| leucine | 18.7 |
| lysine | 23.4 |
| phenylalanine | 13.4 |
| total | 812.2 |

TABLE 2 amino acid analysis of leaves of pepino

| amino acid | content (mg %) (sample of pepino fruit per 100 g) |
|---|---|
| asparagine acid | 285.44 |
| threonine | 62.73 |
| serine | 58.43 |
| glutamine acid | 288.86 |
| proline | 224.11 |
| glycine | 181.47 |
| alanine | 183.46 |
| cysteine | 0.0 |
| valine | 182.67 |
| methionine | 19.26 |
| isoleucine | 149.62 |
| leucine | 271.40 |
| tyrosine | 50.95 |
| phenylalanine | 101.35 |
| lysine | 205.89 |
| histidine | 72.44 |
| arginine | 174.27 |
| total | 2512.35 |

Also, the present invention relates to a method for the preparation of a composition for lowering the concentration of alcohol in blood which comprises 1) extracting the leaves and stalks of the pepino into water or alcohol and obtaining the extracts; 2) after mixing 20 L of these extracts with 30 g of licorice, obtaining the concentrates by concentration; 3) extracting the fruit of the pepino into water or alcohol and obtaining the extracts; 4) mixing 60–70% by weight of the concentrates of step 2) with 30–40% by weight of the extracts of step 3).

In the above, the method of extraction and concentration can be carried out by a well known method in the art. When the blend ratio of the extracts of leaves and stalks of the pepino and licorice is within the above range, the sweet-taste and bilter-taste are in harmony with each other. If the concentrates of step 2) and the extracts of step 3) are used in a blend ratio outside of the above-mentioned range in the composition of the invention, the problems arise as described above.

The composition of the invention can be used as a beverage for curing hangovers, a drug for curing alcoholism or a diet food using dietary fiber. For example, in order to use the composition as a diet food, the concentrates of the above step 2) can be increased to 80 to 90% by weight, decreasing the extracts of the above step 3) to 10–20% by weight and then mixing these. In this case, the composition of the invention can provide food useful for dieting by the action of the dietary fiber aboundantly present in the leaves and stalks of the pepino.

The present invention will be fully illustrated by examples, and the results of an acute toxic test, measurement of antioxidation action and the effect of lowering the concentration of alcohol in the blood by the composition of the invention will be disclosed by experiment.

EXAMPLE

The leaves and stalks of the pepino were washed, then moisture was removed. After finely chopping, the extracts were obtained by extracting the extractor from 10 to 70% of the ethanol from 1 to 10 hours at 30–80° C.

After mixing 20 L of these extracts with 30 g of licorice, the concentrates were obtained by concentration with ordinary method. Apart from this, the extracts of the fruit of the pepino were also obtained by the same manner as the extraction of the leaves and stalks of the pepino. The composition of the invention was obtained by mixing 65% by weight of the extracts of the leaves, stalks and licorice with 35% by weight of the extracts of the fruit. Thus, with the composition prepared in the above manner examples of the administration of the composition are as follows:

Example 1
Acute Toxicity Test (LD50)

After groups of 10 8-week old rats received the composition of the invention in doses of 0.8, 1.6, 3.2, 6.4/kg b.w by oral administration, they were observed by the naked eye to determine the number of dead mice and whether or not any other abnormalities occured at the end of 1 week. The resulting LD50 was more than 6.48 g/kg and there was no abnormalities observed by the naked eye. The results are presented below in Table 3.

TABLE 3 acute toxicity test of the composition of the invention

| | TBA* value by dose | | | | | |
|---|---|---|---|---|---|---|
| Sample | 0 | 0.8 | 1.6 | 3.2 | 6.48 | LD50 |
| Composition of the invention | 0 (0/81) | 3.3 (1/16) | 2.6 (1/39) | 3.7 (2/54) | 0 (0/22) | >6.48 g/kg |

*dose: g/kg
*( ): the number of dead rats/the number of treated rats

Example 2
Measurement of Antioxidation Action (in Vitro Experiment)

Lipid peroxide inhibited action was measured in the liver of the rats. The livers of 15–25 g (weight) male rats is taken, added to 10 ml of 0.9% saline of per 1 g liver, and homonized for 2 min. 0.3 ml of this liver homogenate is mixed with 0.1 ml of the assay solution, and reacted for 5 hour at 37.5° C. TBA indicator was used to dissolve 2-thiobarvituric acid and sodium dodecyl sulfate (SDS) into 7.5% of acetate buffer solution (pH 4.0) in concentrations of 0.3% and 0.4%, respectively. The composition of the invention was used in the concentration of 0.4, 4, 40 mg/ml. A co-test group and a control group were established and the inhibition effect was calculated according to the following equation.

$$\text{inhibition effect (\%)} = \frac{(TBA \text{ value of the control group} - TBA \text{ value of the sample})}{TBA \text{ value of the control group}} \times 100$$

IC50 was obtained by calculating the inhibition ratio relative to each assay solution. The results are shown in Table 4 below.

TABLE 4 inhibition effect in vitro for the lipid and oxidation of the liver of the composition of the invention

| | TBA* value by dose | | | | |
|---|---|---|---|---|---|
| sample | 0 | 0.4 | 4 | 40 | LD50 (mg/ml) |
| composition of the invention | 64.2 | 55.8 (13.1) | 2.6 (38.8) | 28.4 (55.8) | 18.3 |

*TBA value: weight containing the moisture of A535/g liver

The result of the observation, as shown above, of the composition of the invention, showed that the activity of antioxidation, dependent on dose, indicated an inhibited lipid peroxide activity of a maximum of up to 55.8%.

Example 3
Measurement of Antioxidation Action (in vivo Experiment)

After male rats weighing 15–25 g fasted for 24 hours, the composition of the invention was administered orally in the dose form of 0.5, 1, 2, 4 g/kg b.w. for a constant period. Lastly after the specimens were administered, the animals were fasted for 8 hours. Alcohol was administered to the animals at does of 0.52 ml/40 g b.w., respectively. Then after 24 hours, the liver of the rats was removed and the activity of the antioxidation was measured in vivo. The results are shown in Table 5 and FIG. 1 below.

TABLE 5 inhibition effect in vivo for the lipid and oxidation of the liver of the composition of the invention

| sample | TBA value by dose | | | | |
|---|---|---|---|---|---|
| | 0 | 0.5 | 1 | 2 | 4 |
| composition of the invention | 55.4 ± 3.75 | 56.7 ± 7.92 (0) | 44.1 ± 1.50 (20.4) | 41.1 ± 4.07 (25.8) | 38.2 ± 4.79 (31.0) |

As shown above, the composition of the invention, dependent on the dose, inhibited the formation in vivo of lipid oxide by alcohol up to a maximum of 31.0%.

Example 4
Measurement of Effect of Lowering the Concentration of Alcohol in Blood After male rats weighing 150–200 g were fasted for 24 hours, the composition of the invention was administered orally to the rats in the dosage form of 2, 3, 4 g/kg. After 1 hour, ethanol (2.4, 3 g/kg b.w. 30%(w/v H2O) was administered orally. After administration of ethanol, blood was taken from a vein in the tail. Water was fed to the control group of rats which were fasted for 24 hours instead of the composition of the invention; then, after 1 hour, blood was taken by the administration of ethanol.

In order to remove protein in the blood, 0.33M of ice-cold perchloric acid was added to 0.5ml of blood, mixed together, then subjected to centrifuge, and the supernatant liquid was taken. After the supernatant liquid was cooled, stored at −70° C., a concentration of ethanol was measured by an estimation kit (Boehringer Mannheim GmbH). The results are shown in Table 6 and FIGS. 2 and 3 below.

TABLE 6

Effect of lowering the concentration of alcohol in blood

| time | dose (g/kg) | | | |
|---|---|---|---|---|
| (hour) | 0 | 2 | 3 | 4 |
| 0.5 | 2.81 ± 0.17[a] | 1.96** ± 0.19 (30.2)[b] | 2.04** ± 0.12 (27.4) | 2.40* ± 0.09 (14.6) |
| 1 | 4.06 ± 0.21 | 2.44** ± 0.18 (39.9) | 2.46** ± 0.19 (39.4) | 2.00 ± 0.09 (50.7) |
| 2 | 3.35 ± 0.24 | 2.81 ± 0.26 (16.1) | 2.40** ± 0.19 (28.4) | 2.45** ± 0.20 (26.9) |
| 4 | 2.89 ± 0.26 | 2.65 ± 0.32 (8.3) | 2.96* ± 0.21 (32.2) | 1.80 ± 0.20 (37.7) |
| 6 | 2.43 ± 0.29 | 2.05 ± 0.36 (15.6) | 2.81 ± 0.20 (25.5) | 1.64 ± 0.25 (32.5) |
| 8 | 1.97 ± 0.20 | 1.29* ± 0.28 (36.5) | 1.19** ± 0.13 (39.6) | 1.08** ± 0.11 (45.2) |

[a] concentration of alcohol in blood (g/l), mean ± SE from 6–8 rats

[b] inhibition effect (%): $\dfrac{\text{concentration of alcohol in blood (control group} - \text{administration group of the composition)}}{\text{concentration of alcohol in blood of the control group}} \times 100$

*p < 0.05
**p < 0.01

Figure 2:
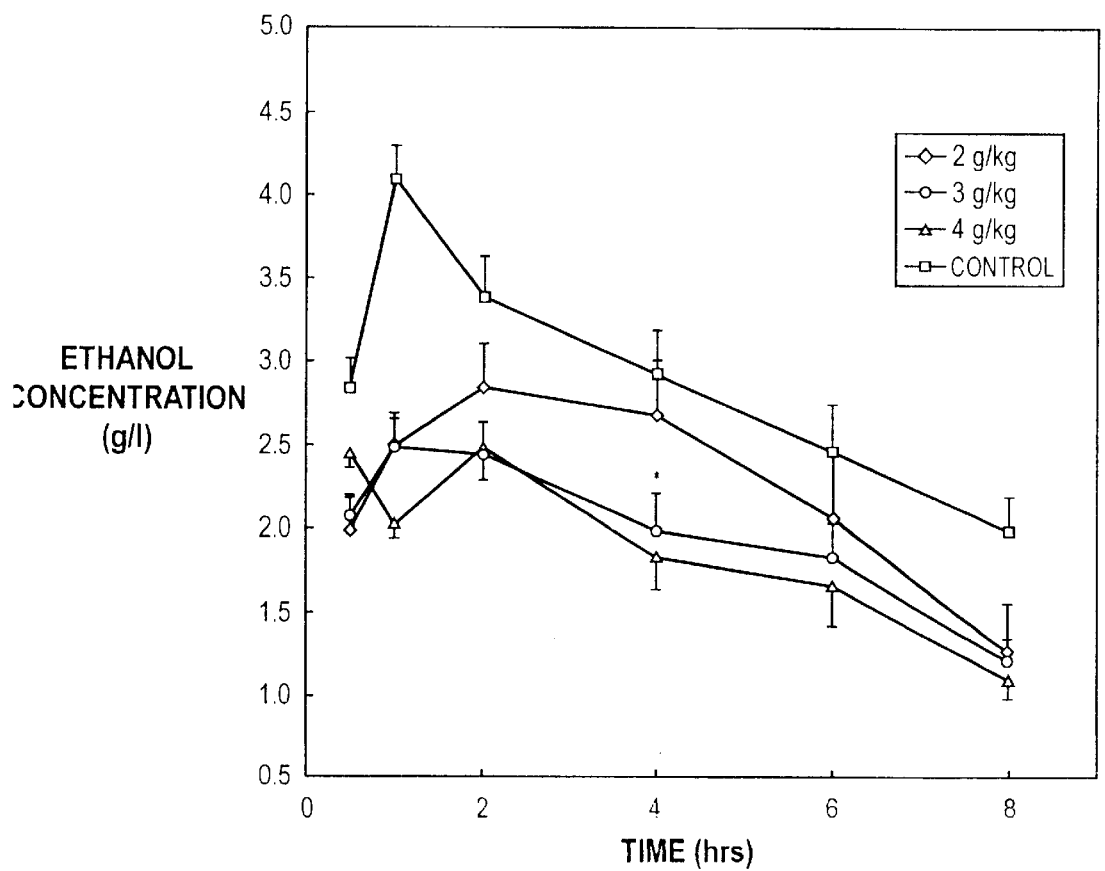
FIGS. 2 and 3 are graphs showing the effect of lowering the concentration of alcohol in the blood with the composition according to the invention.
Figure 3:
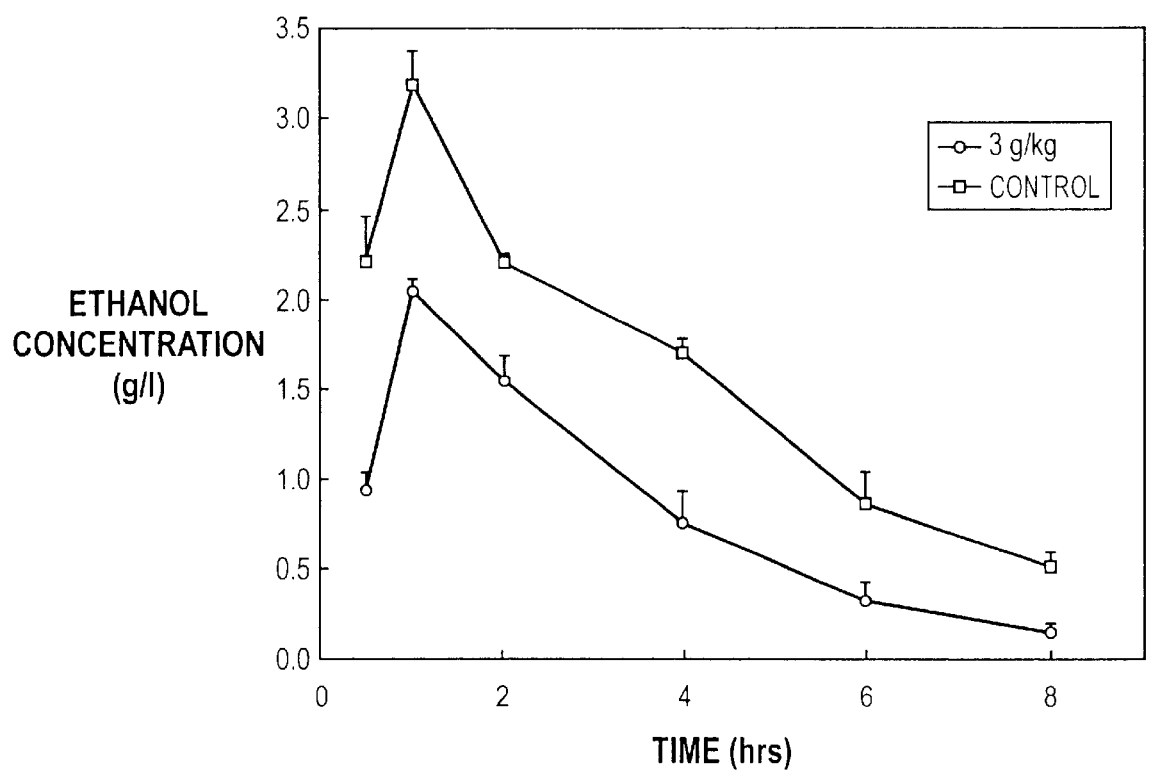

As shown in the above Table 6 and FIGS. 2 and 3, the concentration of alcohol in the blood of the group to which the composition of the invention was administered was much lower than that of the control group.

Results indicate the inhibited formation in vivo of lipid oxide by alcohol, dependent on the dosage up to a maximum of 31.0%. This effect is dependent on dosage. When 3 kg of the composition of the invention was administered to rats per 1 kg body, the result was a maximum 70% effective lowering of the concentration of alcohol in the blood. This effect was clear 1 hour after alcohol was administered at all dosages, and also according to the administration of a dosage, the effect of the concentration of alcohol in the blood was indicated in an inverse variation to the administered alcohol dosage. That is, when the alcohol dosage was 2.4 g/kg in the 3 g/kg dosage of the composition of the invention, the effect of the concentration of alcohol in the blood was about 2 times higher than the alcohol dosage was for 3 g/kg.

The composition of the invention is not acutely toxic and has anti-oxidation action in the liver. The effect of lowering the concentration of alcohol in the blood is excellent; therefore, it is a useful invention available to, for example, food, medicines and the like.

This invention was illustrated in detail in reference with examples, but the skilled person in the art can make changes and variations. It is understood that such changes and variations are within the scope of the invention.

What is claimed is:

1. A composition for lowering the concentration of alcohol in blood which comprises effective amounts of a) extracts from the leaves, stalks and fruit of pepino; and b) licorice.

2. Composition according to claim 1, wherein the leaves and stalks of the pepino are mixed with the licorice and then concentrated.

3. Composition according to claim 2, which comprises 60–70% by weight of the extracts which the leaves and stalk of the pepino and the licorice are mixed together with 30–40% by weight of the extracts of the fruit of the pepino.

4. Composition according to claim 1, which is used for a diet food, beverages and drugs.

5. Composition according to claim 4, which comprises 80–90% by weight of the extracts in which the leaves and stalks of the pepino and the licorice are mixed together with 10–20% by weight of the extracts of the fruit.

6. Composition according to claim 1, which comprises 60–70% by weight of the extracts which the leaves and stalk of the pepino and the licorice are mixed together with 30–40% by weight of the extracts of the fruit of the pepino.

7. A method for the preparation of a composition for lowering the concentration of alcohol in blood which comprises 1) extracting the leaves and stalks of the pepino into water or alcohol and obtaining the extracts; 2) after mixing 20 L of these extracts with 30 g of licorice, obtaining the concentrate by concentration; 3) extracting the fruit of the pepino into water or alcohol obtaining the extract and; 4) mixing 60–70% by weight of the concentrate of step 2 with 30–40% by weight of the extract of step 3.

* * * * *